(12) United States Patent  
Kim et al.

(10) Patent No.: US 8,798,698 B2  
(45) Date of Patent: Aug. 5, 2014

(54) APPARATUS AND METHOD OF PROCESSING PLURALITY OF BIOLOGIC SIGNALS

(75) Inventors: Youn-ho Kim, Hwaseong-si (KR); Jong-keun Song, Yongin-si (KR); Dong-wook Kim, Seoul (KR); Kun-soo Shin, Seongnam-si (KR); Hyung-sok Yeo, Yongin-si (KR); Sang-kon Bae, Seongnam-si (KR); Woo-young Jang, Seongnam-si (KR); Ji-hoon Kim, Seoul (KR)

(73) Assignee: Samsung Electronics Co., Ltd. (KR)

( * ) Notice: Subject to any disclaimer, the term of this patent is extended or adjusted under 35 U.S.C. 154(b) by 836 days.

(21) Appl. No.: 12/609,116

(22) Filed: Oct. 30, 2009

(65) Prior Publication Data

US 2010/0113898 A1    May 6, 2010

(30) Foreign Application Priority Data

Oct. 30, 2008    (KR) .................. 10-2008-0107422

(51) Int. Cl.
*A61B 5/00*    (2006.01)

(52) U.S. Cl.
USPC ......................................... 600/310

(58) Field of Classification Search
USPC ......................................... 600/310
See application file for complete search history.

(56) References Cited

U.S. PATENT DOCUMENTS

| | | | | |
|---|---|---|---|---|
| 5,307,263 | A * | 4/1994 | Brown | 600/301 |
| 5,623,925 | A * | 4/1997 | Swenson et al. | 600/301 |
| 5,687,717 | A * | 11/1997 | Halpern et al. | 600/300 |
| 5,701,894 | A * | 12/1997 | Cherry et al. | 600/300 |
| 2007/0142718 | A1 * | 6/2007 | Abreu | 600/323 |
| 2008/0188729 | A1 * | 8/2008 | Sato et al. | 600/340 |

* cited by examiner

*Primary Examiner* — Clayton E Laballe
*Assistant Examiner* — Fang-Chi Chang
(74) *Attorney, Agent, or Firm* — Cantor Colburn LLP

(57) ABSTRACT

An apparatus for integrally processing a plurality of biologic signals includes a first signal processing module and a second signal processing module. The first processing module generates a signal for operating a sensing module, which includes a plurality of sensor groups which measures the plurality of biologic signals, and which processes a biologic signal provided from the plurality of sensor groups based on a control signal. The second signal processing module authenticates a sensor group from among the plurality of sensor groups, generates the control signal according to a result of the authentication while automatically setting a processing condition, processes the biologic signal provided from the first signal processing module according to the processing condition and outputs a result of processing the biologic signal.

17 Claims, 12 Drawing Sheets

FIG. 11
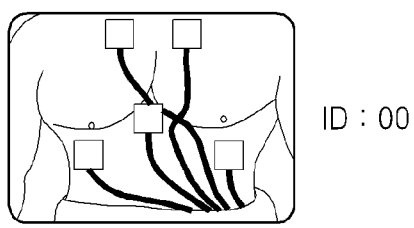
ID : 00
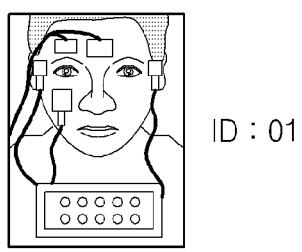
ID : 01
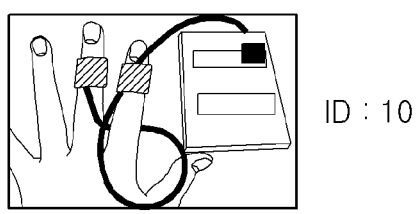
ID : 10
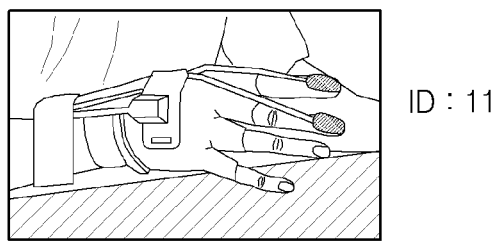
ID : 11

APPARATUS AND METHOD OF PROCESSING PLURALITY OF BIOLOGIC SIGNALS

CROSS-REFERENCE TO RELATED APPLICATION

This application claims priority to Korean Patent Application No. 10-2008-0107422, filed on Oct. 30, 2008, and all the benefits accruing therefrom under 35 U.S.C. §119, the content of which in its entirety is herein incorporated by reference.

BACKGROUND

1. Field

The general inventive concept relates to an apparatus and method of integrally processing a plurality of biologic signals.

2. Description of the Related Art

Generally, to measure a biologic ("bio") potential signal, such as in an electrocardiogram, an electroencephalogram, an electromyogram, an electrooculogram or for an electrogastrography signal, for example, a filter having a filtered frequency band corresponding to a type of the measured bio potential signal is used. However, a conventional filter is able to perform filtering in only one frequency band. Accordingly, to measure a plurality of bio potential signals with a single device, a required number of filters is at least as many as a number of the plurality of bio potential signals to be measured. As a result, when the single device manufactured to measure various types of bio potential signals, a number of parts required in the single device increases. Thus, power consumption of the single device increases, manufacturing costs of the same increase, and it is difficult to miniaturize the device.

In addition, an impedance related to body fat, skin hydration or skin conductance level, for example, is often measured. As a result, a desired signal is typically detected by rectifying a constant current having a frequency corresponding to a specific type of impedance, and a signal is thereby obtained via differential amplification. The constant current and the signal are then filtered. In a conventional device, a process of measuring the impedance is complicated, since only one signal is measured, according to a determined frequency, but additional constant current needs to be applied, unlike when a bio potential signal is measured, as discussed above. As a result, the required number of parts further increases due to the complicated process of measuring impedance. Accordingly, power consumption and manufacturing costs further increase, while miniaturization is made even more difficult.

Additionally, to measure a bio signal using light, such for as a pulse wave signal or oxygen saturation, for example, light having a specific wavelength that corresponds to the measured bio signal is irradiated and, thus, a typical conventional device is able to measure only one bio signal.

Accordingly, there is a need to develop a single device that measures more than one bio signal.

SUMMARY

One or more embodiments include an apparatus and method of integrally processing a plurality of biologic ("bio") signals, wherein the plurality of bio signals are processed using only one device.

One or more embodiments include an apparatus for integrally processing a plurality of bio signals. The apparatus includes a first signal processing module and a second signal processing module. The first processing module generates a signal for operating a sensing module, which includes a plurality of sensor groups which measures the plurality of biologic signals, and which processes a biologic signal provided from the plurality of sensor groups based on a control signal. The second signal processing module authenticates a sensor group from among the plurality of sensor groups, generates the control signal according to a result of the authentication while automatically setting a processing condition, processes the biologic signal provided from the first signal processing module according to the processing condition and outputs a result of processing the biologic signal.

One or more alternative embodiments include a method of integrally processing a plurality of bio signals, the method including: generating a signal for operating each sensor group of a plurality of sensor groups of a sensing module which measures the plurality of bio signals and processes a bio signal provided from each of the sensor groups based on a control signal; authenticating a sensor group used from among the plurality of sensor groups; generating the control signal according to a result of the authenticating while automatically setting a processing condition; processing a provided biologic signal according to the processing condition; and outputting a result of the processing.

One or more alternative embodiments provide a computer program product including a computer readable program code for executing a method of integrally processing a plurality of biologic signals and instructions for causing a computer to implement the method. The method includes: generating a signal for operating each sensor group of a plurality of sensor groups of a sensing module which measures the plurality of biologic signals and processes a biologic signal provided from each of the sensor groups based on a control signal; authenticating a sensor group used from among the sensor groups of the plurality of sensor groups; generating the control signal according to a result of the authenticating while automatically setting a processing condition; processing a provided biologic signal according to the processing condition; and outputting a result of the processing.

BRIEF DESCRIPTION OF THE DRAWINGS

The above and/or other aspects and features will become more readily apparent and more readily appreciated be describing embodiments of the general inventive concept in further detail with reference the accompanying drawings, in which:

FIG. 11 is a diagram illustrating embodiments of unique identification code information assigned to authenticate an electrode and sensing channel of an embodiment of an apparatus and method of integrally processing a plurality of bio signals.

DETAILED DESCRIPTION

Figure 1:
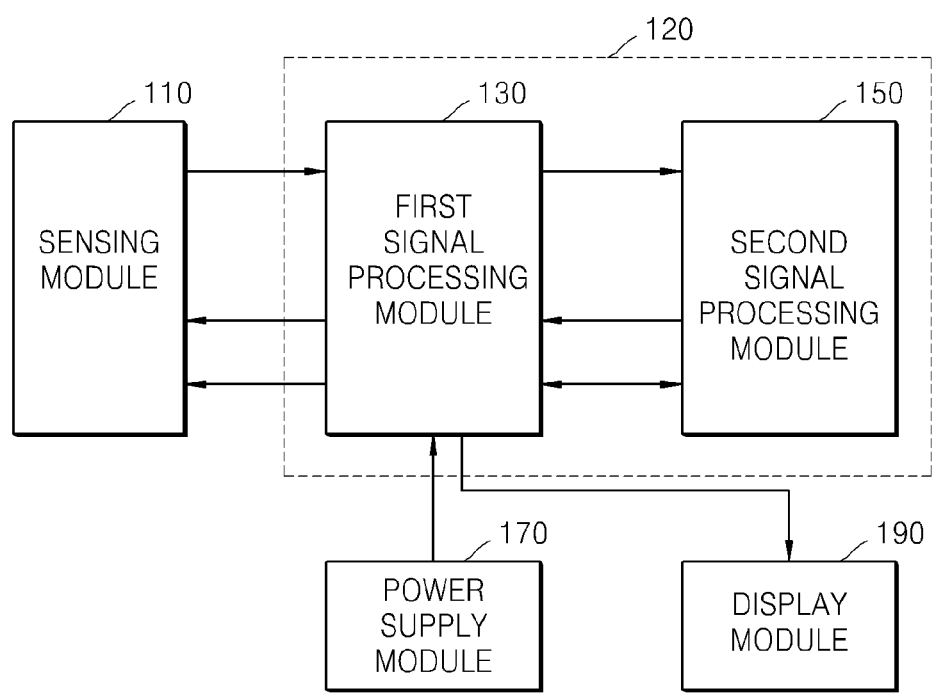
FIG. 1 is a block diagram illustrating an embodiment of an apparatus for integrally processing a plurality of biologic ("bio") signals.

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings herein.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Hereinafter, embodiments will be described in further detail with reference to the accompanying drawings.

FIG. 1 is a block diagram illustrating an embodiment of an apparatus for integrally processing a plurality of biologic ("bio") signals. The apparatus includes a first signal processing module 130 and a second signal processing module 150. Alternatively, the apparatus may include a sensing module 110, the first signal processing module 130 and the second signal processing module 150, but additional alternative embodiments are not limited thereto. In an embodiment, the first signal processing module 130 may be wirelessly connected to the sensing module 110 or connected via a wire (not shown) to the sensing module 110, such as via an attachable jack and/or a cord, for example. In addition, the first signal processing module 130 may be wirelessly connected to a power supply module 170, or connected via a wire to the power supply module 170, such as via an attachable jack and/or a cord, for example (hereinafter referred to as "wire-connected"). Likewise, the first signal processing module 130 may be wirelessly connected to a display module 190, or wire-connected to the display module 190. Similarly, the second signal processing module 150 may be wirelessly connected to the display module 190, or wire-connected to the display module 190. Additionally, the display module 190 may be connected to the second signal processing module 150, instead of the first signal processing module 130, wirelessly or via wires (not shown). In an embodiment, the first signal processing module 130 and the second signal processing module 150 may be implemented via a processor, such as a central processing unit ("CPU") in a micro-computer, for example, and/or may be implemented as one chip 120 as a system on chip ("SOC").

Referring still to FIG. 1, the sensing module 110 may include one of a first sensor group for measuring a potential signal, a second sensor group for measuring impedance, and a third sensor group for measuring a bio signal obtained from light, or at least two thereof, as will be described in further detail below. Each sensor group of the sensing module 110 is not particularly limited and may vary, for example, to be in a device that is attached to skin, a device that is put on a finger, or in the form of a glove. In an embodiment, the sensing module 110 includes the first sensor group, the second sensor group and the third sensor group (as will be described in further detail below); however, alternative embodiments are not limited thereto, and thus, the sensing module 110 may further include a sensor group for detecting a motion signal, for example.

The first signal processing module 130 determines whether to apply a trigger signal to the sensing module 110. The trigger signal corresponds to a type of a bio signal that is to be processed. The first signal processing module 130 also pre-process a plurality of sensing channel signals, provided from the sensing module 110, and generates an intermediate bio signal that is amplified by a predetermined gain according to a result of the pre-processing. The trigger signal may be a current signal, but is not limited thereto. In addition, the first signal processing module 130 may generate the trigger signal from a power supply voltage supplied from the power supply module 170, and provide the trigger signal to each sensing channel connected to the sensing module 110, and determine a fault of a lead by measuring an impedance of each sensing channel or transmit the trigger signal to the sensing module 110 to obtain an impedance signal or a bio signal using light (for example).

The second signal processing module 150 may automatically set a processing condition according to a type of a bio signal to be processed, generate a final bio signal by filtering and amplifying the intermediate bio signal provided from the first signal processing module 130 according to the processing condition, and process the final bio signal by using an arithmetic algorithm, for example, corresponding to an application field. A result of the processing may be stored in an internal memory, provided to the first signal processing module 130, provided to the display module 190, or transmitted to an external memory, while alternative embodiments are not limited thereto.

The power supply module 170 may apply a power supply voltage to the first signal processing module 130 and/or to the second signal processing module 150, and generate the trigger signal which the sensing module 110 uses to obtain the impedance signal or the bio signal using light, such as a predetermined current signal.

The display module 190 may display a result of processing a signal provided from the second signal processing module 150, thereby providing corresponding analysis information to a user.

Thus, in the single apparatus of FIG. 1, at least two signals of a bio potential signal, an impedance signal, a motion signal and a bio signal using light may be measured and analyzed. As described above, when a bio signal to be processed is determined, a processing condition is automatically set, and thus a bio potential signal, an impedance signal, a motion signal and a bio signal using light are all measured by using one simple device, and the apparatus for integrally processing the plurality of bio signals may therefore be made smaller, e.g., miniaturized, while power consumption of the apparatus is substantially reduced. Accordingly, it is convenient to manufacture the apparatus as a portable device, and to install the apparatus in a mobile device or other type of device, for that matter. Moreover, while processing the bio signal, required manipulation or participation of a user is effectively minimized, and thus any error caused by the user is minimized.

Figure 2:
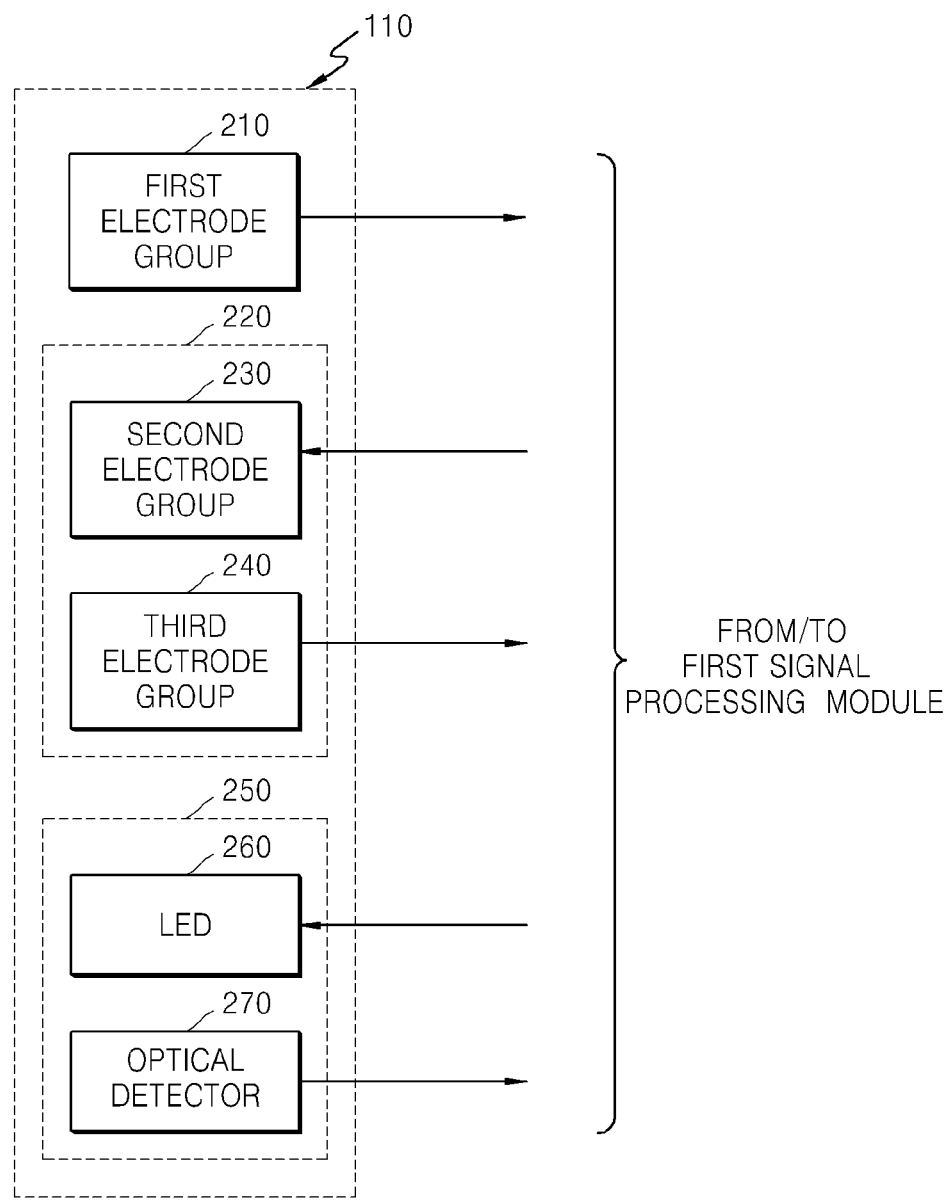
FIG. 2 is a block diagram illustrating a sensing module of the apparatus illustrated in FIG. 1.

FIG. 2 is a block diagram illustrating an embodiment of the sensing module 110 of the apparatus illustrated in FIG. 1. The sensing module 110 may include a first electrode group 210 for measuring a bio potential signal. In an embodiment, the first electrode group 210 is a first sensor group 210. In addition, the sensing module 110 includes a second sensor group 220 for measuring an impedance signal, and a third sensor group 250 for measuring a bio signal using light. In an embodiment, the second sensor group 220 includes a second electrode group 230, to which a constant current is applied, and a third electrode group 240, to which an impedance signal is outputted, while the third sensor group 250 includes a light emitting diode ("LED") 260, to which a predetermined driving current is applied and an optical detector 270, from which a photoplethysmography signal is outputted. In an alternative embodiment, the sensing module 110 may further include an accelerometer (not shown) for measuring a motion signal.

The first electrode group 210, which in an embodiment is the first sensor group 210, may be an electrocardiogram ("ECG") sensor, for example. The ECG sensor senses the ECG by measuring a heartbeat of a user by placing the ECG sensor on the user's chest, or from sensors on the user's forearms and/or hands. A number, shape and placement of electrodes included in the first electrode group 210 may vary, and an attaching location of the first electrode group 210 may also vary in alternative embodiments.

When a constant current, for example, a current of about 1 milliampere (mA) is applied to the second electrode group 230 in a frequency band of 50 kilohertz (kHz), for example, to measure impedance, a predetermined voltage is generated in the third electrode group 240.

In alternative embodiments, the number and shape of electrodes included in the second electrode group 230 and the third electrode group 240 may vary, as can their attaching locations.

The optical detector 270 of the third sensor group 250 is attached to the user's skin of a fingertip or toe tip, for example to measure photoplethysmography in the skin tissue. Specifically, the LED 260 irradiates infrared rays onto the skin tissue, and the optical detector 270 measures an intensity of the infrared rays absorbed by the skin tissue, and thus a change of blood amount in the skin tissue is detected. The third sensor group 250 uses a characteristic of red blood cells in the blood (that absorb infrared rays) to measure the amount of blood flowing into a capillary via an artery and an arteriole, and determines whether the bloodstream at the peripheries, such as the fingertips and toe tips, is acceptable.

Figure 3:
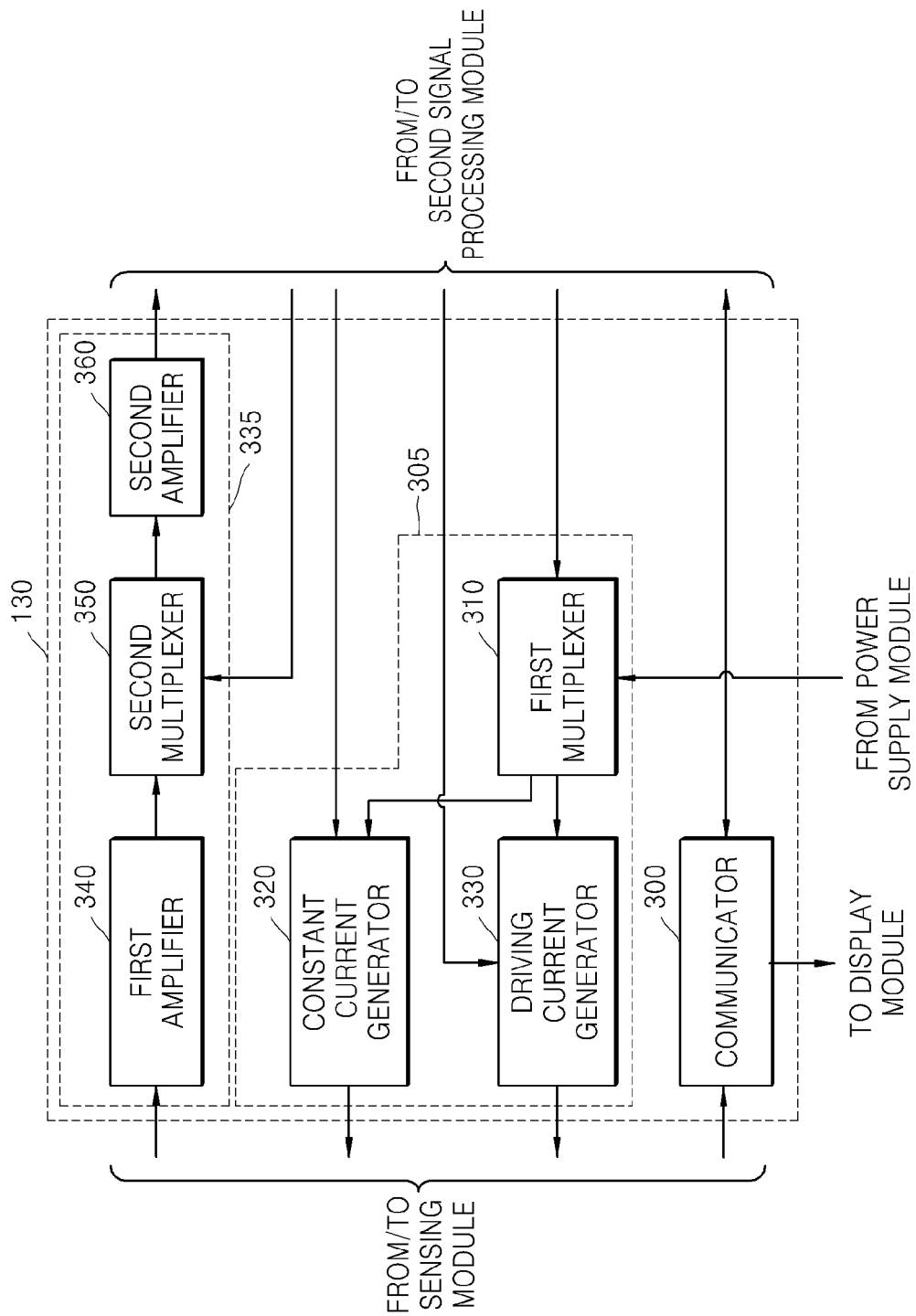
FIG. 3 is a block diagram illustrating a first signal processing module of the apparatus illustrated in FIG. 1.

FIG. 3 is a block diagram illustrating an embodiment of the first signal processing module 130 of the apparatus illustrated in FIG. 1. The first signal processing module 130 may include a communicator 300, a trigger signal generator 305 and an intermediate bio signal generator 335. The trigger signal generator 305 may include a first multiplexer 310, a constant current generator 320 and a driving current generator 330. The intermediate bio signal generator 335 may include a first amplifier 340, a second multiplexer 350 and a second amplifier 360.

Figure 4:
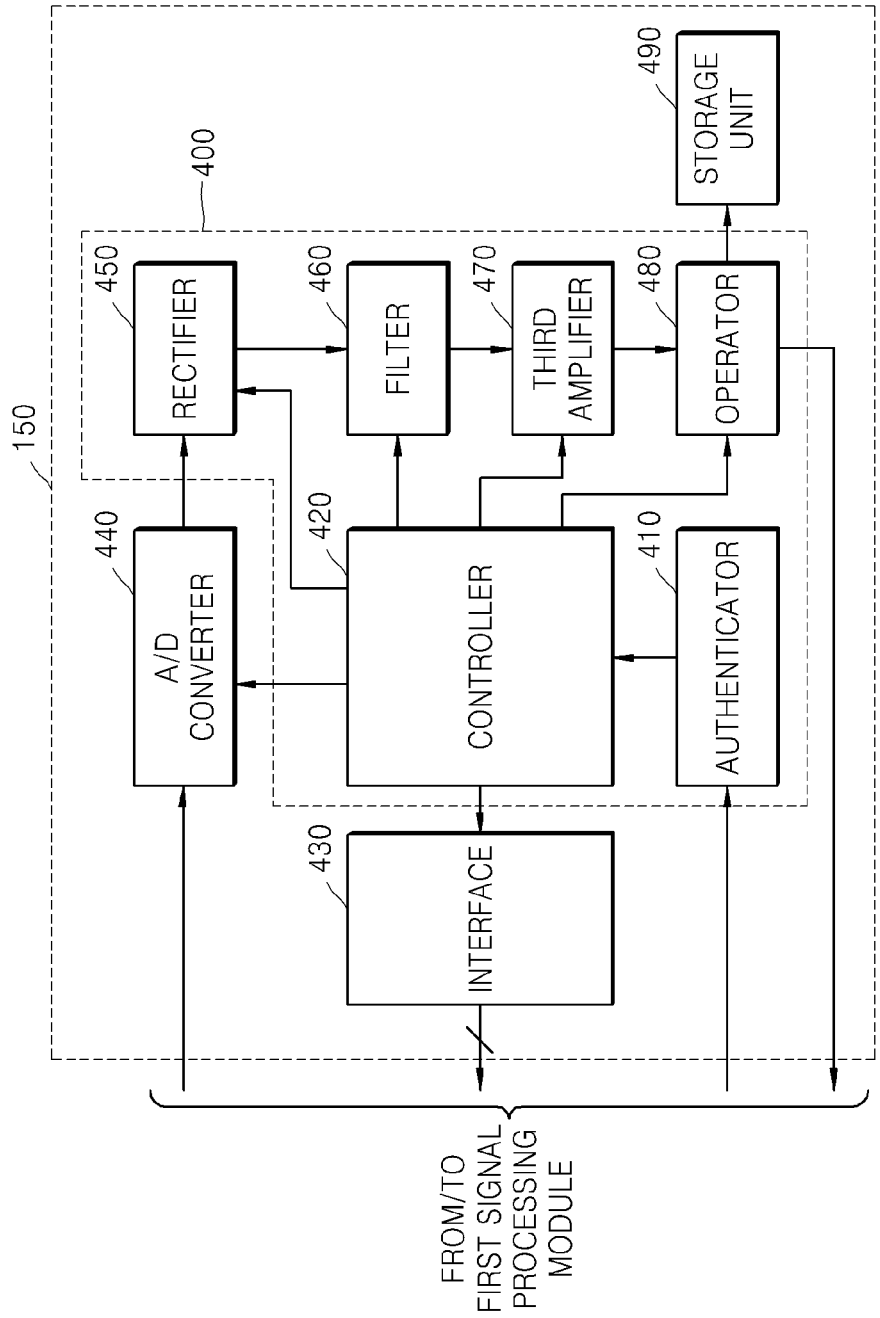
FIG. 4 is a block diagram illustrating a second signal processing module of the apparatus illustrated in FIG. 1.

Referring now to FIG. 3, the communicator 300 receives unique identification ("ID") code information transmitted from each of the first, second and third sensor groups 210, 220 and 250, respectively, of the sensing module 110 wirelessly or via wires, and transmits the received unique ID code information to an authenticator 410 of the second signal processing module 150 (FIG. 4). Specifically, when the communicator 300 operates wirelessly, the unique ID code information is assigned to each of the first, second and third sensor groups 210, 220 and 250, respectively, of the sensing module 110, and when each of the first, second and third sensor groups 210, 220 and 250, respectively, is used, the unique ID code information changes to an active state, and is wirelessly provided to the communicator 300. Thus, the unique ID code information may be communicated via a short distance communication between the sensing module 110 and the communicator 300, and radio frequency identification ("RFID") techniques may be used for the same, for example. Alternatively, when the communicator 300 operates via wires, the communicator 300 may include a plurality of connectors (not shown), for example, each of which includes pins at locations corresponding to each electrode included in each electrode group of the first, second and third sensor groups 210, 220 and 250, respectively, of the sensing module 110. In this case, since the unique ID code information is assigned to each connector, when an electrode is connected to one connector, the recognized ID code information corresponding to the connector is provided to the second signal processing module 150 via the communicator 300. Also, the communicator 300 receives a result operation performed by an operator 480 of the second signal processing module 150 (FIG. 4), and outputs the received result wirelessly or, alternatively, via wires. More particularly, the display module 190 may provide the result to an external medical institution, such as a hospital (not shown), for example.

The trigger signal generator 305 generates a trigger signal from a power supply voltage provided from the power supply module 170 and provides the trigger signal to the sensing module 110, which corresponds to a type of a bio signal to be processed. Thus, the trigger signal may be used to determine a fault in a lead of an electrode included in each of the first, second and third sensor groups 210, 220 and 250, respectively. When the sensing module 110 and the communicator 300 communicate via wire, the trigger signal, such as a constant current, for example, is provided to the each of the first, second and third sensor groups 210, 220 and 250, respectively, via the respective connector of the communicator 300 and the constant current generator 320. When the sensing module 110 and the communicator 300 perform wireless communication, the trigger signal may be directly provided to each of the first, second third sensor groups 210, 220 and 250, respectively, via the constant current generator 320. A method of determining a fault in a lead is not limited to the foregoing description, and thus may vary in alternative embodiments. The trigger signal may be used to obtain a certain bio signal, such as an impedance signal or a photoplethysmography signal, for example.

More specifically, the first multiplexer 310 applies a power supply voltage provided from the power supply module 170 to at least one of the constant current generator 320 and the driving current generator 330 or, alternatively, blocks the power supply voltage, according to a type of the bio signal to be processed, by using a first control signal provided from an interface 430 of the second signal processing module 150. Thus, when the bio signal to be processed is determined, the second signal processing module 150 recognizes a connection status of the sensing module 110, the first control signal is used to determine the fault of a lead by applying the power supply voltage to the constant current generator 320 and then applies or blocks the power supply voltage according to the bio signal to be processed.

The constant current generator 320 generates a constant current which measures an impedance signal, corresponding to a second control signal provided from the interface 430 and an output signal of the first multiplexer 310. The constant current generator 320 is connected to each electrode of the sensing module 110, and may apply the constant current to determine a fault in a lead of each electrode. Here, the second control signal is used to adjust an amplitude of the constant current according to a type of impedance to be processed.

The driving current generator 330 generates a driving current which measures a bio signal using light, corresponding to a third control signal provided from the interface 430 and an output signal of the first multiplexer 310. Here, the third control signal is used to adjust a wavelength or an amplitude of the driving current according to a type of the bio signal using light, such as bio signals for detecting hemoglobin or glucose levels, for example.

The intermediate bio signal generator 335 generates an intermediate bio signal from a bio signal provided from the sensing module 110. Specifically, the first amplifier 340 amplifies a bio signal provided from each sensing channel of the sensing module 110. Here, to prevent signal distortion that may be generated in the second multiplexer 350, the first amplifier 340 may perform an auto-zeroing function that adjusts a voltage range inputted to the second multiplexer 350 and/or may remove direct current ("DC") noise generated in each electrode or the skin, for example.

The second multiplexer 350 multiplexes an output of each electrode provided from the first amplifier 340 and provides the multiplexed output to the second amplifier 360, corresponding to a fourth control signal provided from the interface 430 of the second signal processing module 150. In an embodiment, the fourth control signal is used to determine a processing order of the output of each electrode according to the type of the bio signal to be processed. In other words, when the type of the bio signal to be processed is determined in the second signal processing module 150, a used sensor group is determined. The second multiplexer 350 sets a signal path between the first amplifier 340 and the second amplifier 360 based on preset priority of each electrode included in the determined sensor group.

The second amplifier 360 generates the intermediate bio signal by amplifying the output of each electrode provided from the second multiplexer 350, and transmits the intermediate bio signal to an analog/digital ("A/D") converter 440 of the second signal processing module 150 (FIG. 4).

FIG. 4 is a block diagram illustrating an embodiment of the second signal processing module 150 of the apparatus illustrated in FIG. 1. The second signal processing module 150 may include a signal processor 400, the interface 430, an A/D converter 440 and a storage unit 490. The signal processor 400 may include the authenticator 410, a controller 420, a rectifier 450, a filter 460, a third amplifier 470 and the operator 480. The second signal processing module 150 may be a micro controller unit ("MCU"), but alternative embodiments are not limited thereto.

Referring to FIG. 4, the signal processor 400 automatically sets a processing condition and operation program according to the type of the bio signal to be processed, and generates the first through fourth control signals for controlling the first signal processing module 130. More particularly, the authenticator 410 authenticates a sensing group to be used by using the unique ID code information provided via the communicator 300, and transmits a result of the authentication to the controller 420 so that a frequency band to be measured and an amplification gain are adjusted according to the authenticated sensing group.

The controller 420 sets an ND conversion condition, a filtering band, an amplification gain, and an arithmetic algorithm according to the result of the authentication of the authenticator 410, while controlling the interface 430. Under the control of the controller 420, the rectifier 450 rectifies a digital bio signal. Here, when the apparatus is used to measure impedance, for example, the rectifier 450 operates, but when the apparatus is used to measure a bio potential signal, the rectifier 450 is programmed to not operate. Thus, under the control of the controller 420, the filter 460 filters the bio signal rectified by the rectifier 450. Accordingly, a frequency band to be filtered is set based on the result of the authentication of the authenticator 410.

Under the control of the controller 420, the third amplifier 470 amplifies the bio signal filtered in the filter 460. Specifically, an amplification gain is set according to the result of the authentication of the authenticator 410. Under the control of the controller 420, the operator 480 obtains bio information of a desired application field according to the bio signal, by operating a predetermined arithmetic algorithm on the bio signal amplified by the third amplifier 470. The bio information is provided to the communicator 300 of the first signal processing module 130, and/or is stored in the storage unit 490.

Under the control of the controller 420, the interface 430 generates and outputs the first through fourth control signals for each unit of the first signal processing module 130.

Under the control of the controller 420, the ND converter 440 converts the bio signal provided from the second amplifier 360 of the first signal processing module 130 into a digital signal.

The storage unit 490 stores the bio information obtained from the operator 480.

Figure 5:
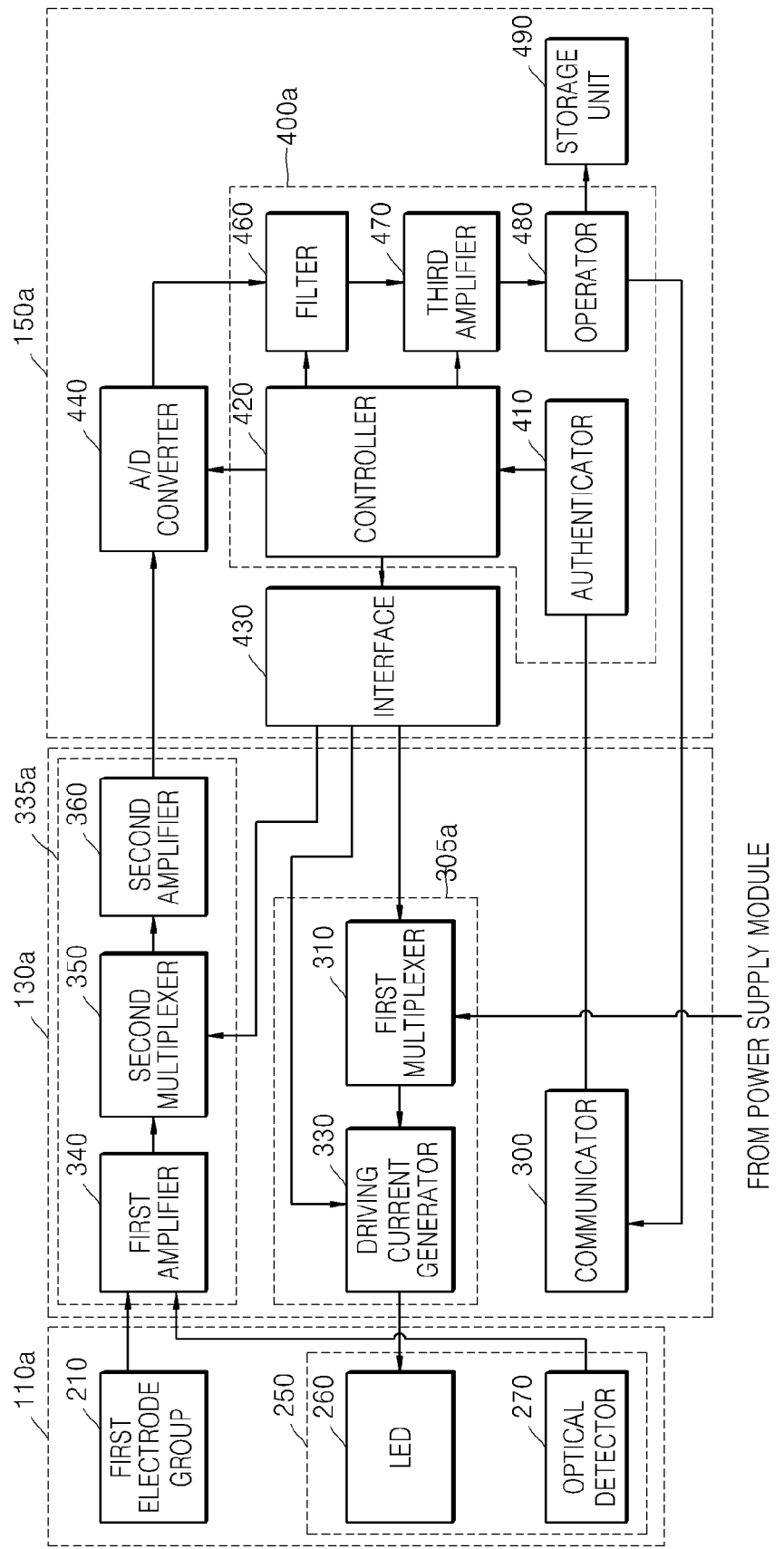
FIG. 5 is a block diagram illustrating an embodiment of a dedicated chip for an apparatus for monitoring a patient by using an embodiment of an apparatus for integrally processing a plurality of bio signals.

FIG. 5 is a block diagram illustrating an embodiment of a dedicated chip for an apparatus for monitoring a patient by using an embodiment of an apparatus for integrally processing a plurality of bio signals. In FIG. 5, as well as subsequent figures, the same or like components are labeled with same reference characters used and described in greater detail above with reference to embodiments shown in the previous figures, and any repetitive detailed description thereof will hereinafter be simplified or omitted.

Referring now to FIG. 5, a sensing module 110a includes the first electrode group 210, which is the first sensor group 210 (as discussed above), and the third sensor group 250. A first signal processing module 130a includes the communicator 300, a trigger signal generator 305a and an intermediate bio signal generator 335a. In an embodiment, the trigger signal generator 305a includes the first multiplexer 310 and the driving current generator 330, and the intermediate bio signal generator 335a includes the first amplifier 340, the second multiplexer 350 and the second amplifier 360. A second signal processing module 150a includes a signal processor 400a, the interface 430, the ND converter 440 and the storage unit 490. The signal processor 400a includes the authenticator 410, the controller 420, the filter 460, the third amplifier 470 and the operator 480.

In an embodiment, the dedicated chip for the apparatus for monitoring a patient illustrated in FIG. 5 simultaneously measures temperature, an electrocardiogram, oxygen saturation and respiration, for example, and the dedicated chip is therefore not only capable of being in a medical institution like a hospital, but may also be applied to a wearable monitor to monitor an urgent patient or a patient with deteriorated health in the patient's home, for example.

Figure 6:
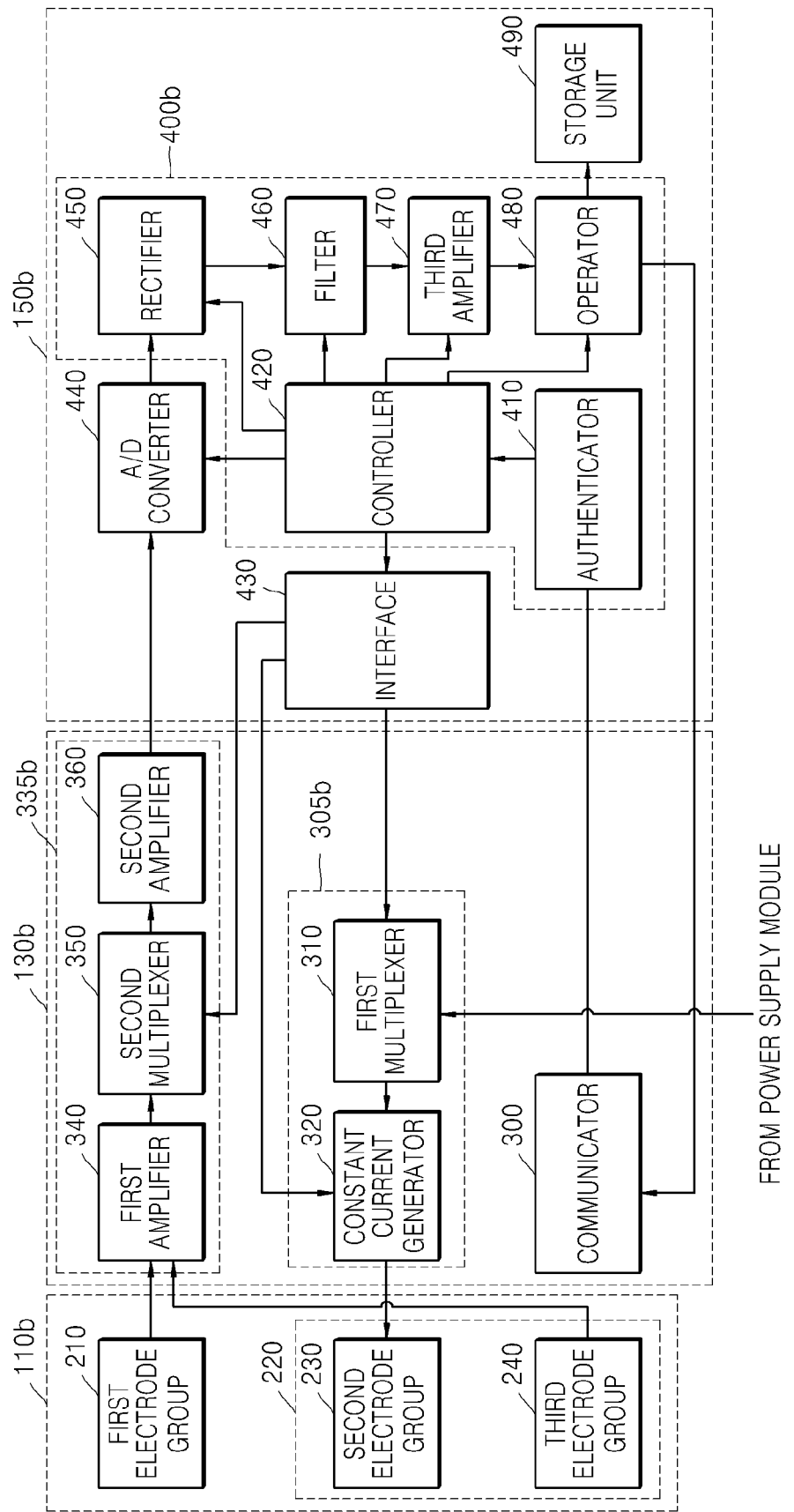
FIG. 6 is a block diagram illustrating an alternative embodiment of a dedicated chip for an apparatus for processing impedance and potential by using an embodiment of an apparatus for integrally processing a plurality of bio signals.

FIG. 6 is a block diagram illustrating an alternative embodiment of a dedicated chip for an apparatus for processing impedance and potential by using an embodiment of an apparatus for integrally processing a plurality of bio signals.

Referring to FIG. 6, a sensing module 110b includes the first electrode group 210 (which is the first sensor group 210) and the second sensor group 220. A first signal processing module 130b includes the communicator 300, a trigger signal generator 305b and an intermediate bio signal generator 335b. In an embodiment, the trigger signal generator 305b includes the first multiplexer 310 and the constant current generator 320, and the intermediate bio signal generator 335b includes the first amplifier 340, the second multiplexer 350 and the second amplifier 360. A second signal processing module 150b includes a signal processor 400b, the interface 430, the ND converter 440 and the storage unit 490. The signal processor 400b includes the authenticator 410, the controller 420, the rectifier 450, the filter 460, the third amplifier 470 and the operator 480.

The dedicated chip illustrated in FIG. 6 simultaneously measures signals such as body fat and skin conductance level, for example.

Figure 7:
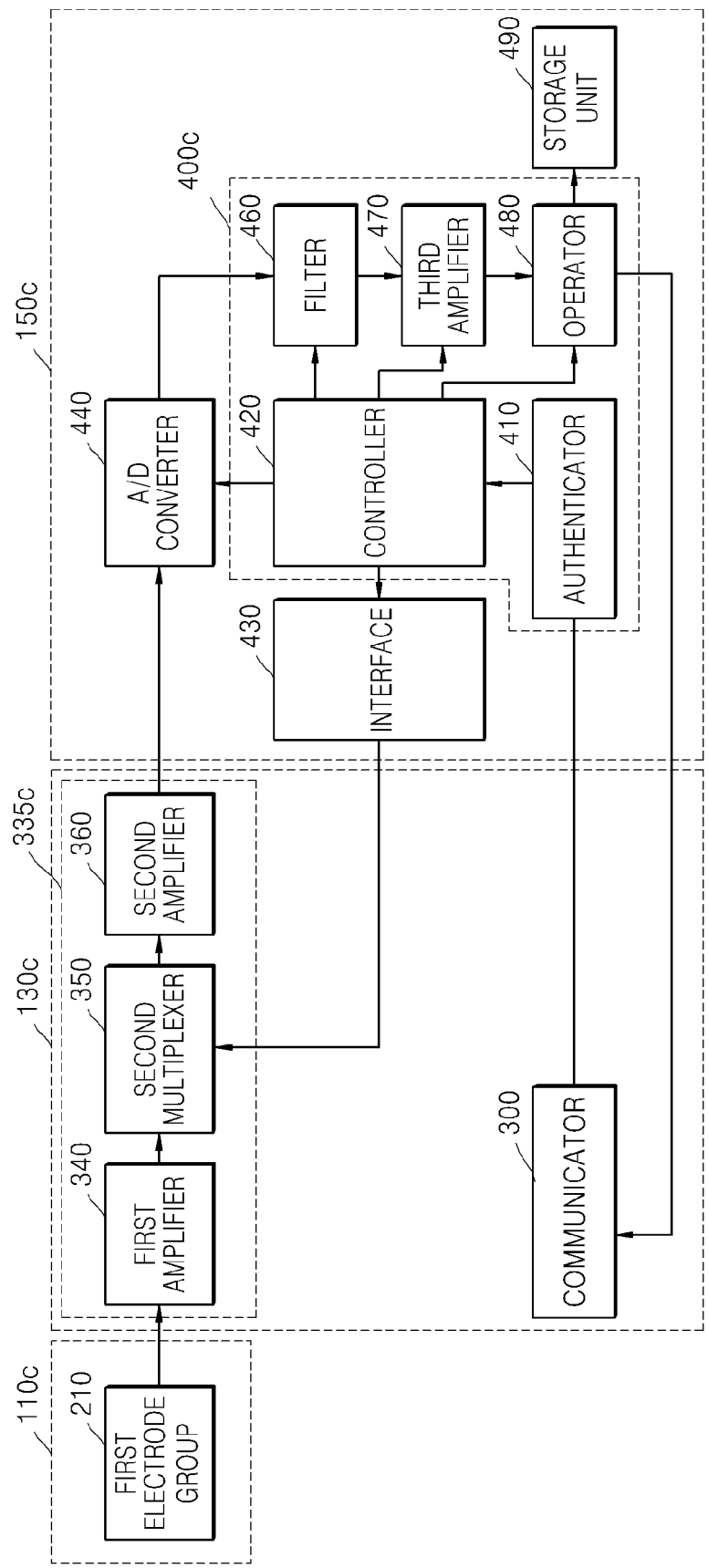
FIG. 7 is a block diagram illustrating an alternative embodiment of a dedicated chip for an apparatus for processing potential by using an embodiment of apparatus for integrally processing a plurality of bio signals.

FIG. 7 is a block diagram illustrating an alternative embodiment of a dedicated chip for an apparatus for processing potential by using an embodiment of apparatus for integrally processing a plurality of bio signals.

Referring to FIG. 7, a sensing module 110c includes the first electrode group 210 (e.g., the first sensor group 210). A first signal processing module 130c includes the communicator 300 and an intermediate bio signal generator 335c. The intermediate bio signal generator 335c includes the communicator 300, the first amplifier 340, the second multiplexer 350 and the second amplifier 360. A second signal processing module 150c includes a signal processor 400c, the interface 430, the A/D converter 440 and the storage unit 490. The signal processor 400c includes the authenticator 410, the controller 420, the filter 460, the third amplifier 470 and the operator 480.

The dedicated chip illustrated in FIG. 7 simultaneously measures potential signals such as an electrocardiogram, an electromyogram and brain waves, for example.

Referring to FIGS. 5 through 7, the first through fourth control signals for controlling the sensing module 110 and the first signal processing module 130 are generated according to a bio signal to be processed, and an optimum processing condition of a bio signal of the second signal processing module 150 is automatically set, and thus bio information of a desired application field is generated by processing an intermediate bio signal outputted through the sensing module 110 and the first signal processing module 130 according to the set optimum processing condition.

Figure 8:
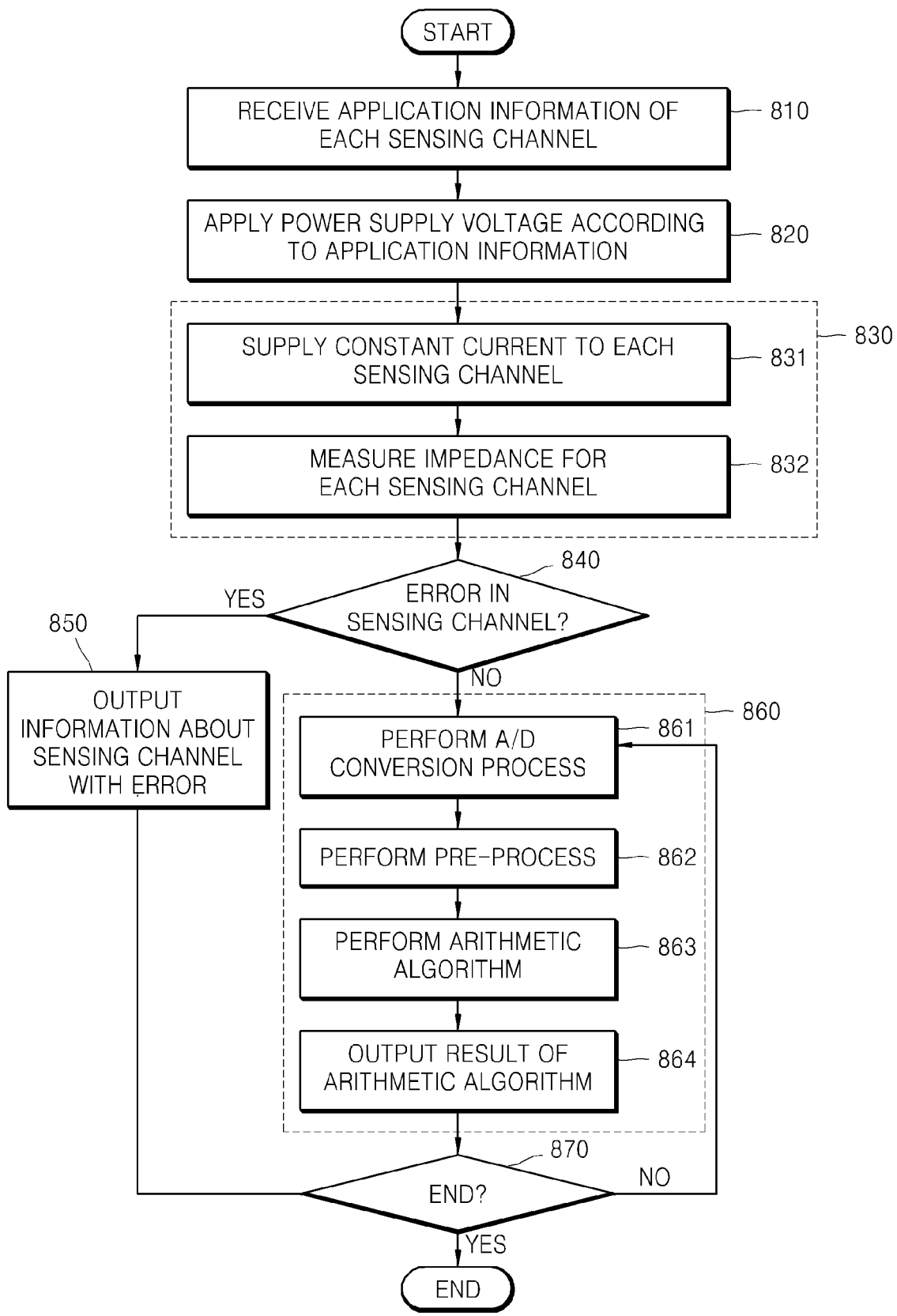
FIG. 8 is a flowchart illustrating an embodiment of a method of integrally processing a plurality of bio signals.

FIG. 8 is a flowchart illustrating an embodiment of a method of integrally processing a plurality of bio signals.

Referring to FIG. 8, application information of each sensing channel is received in operation 810. The application information may be received via a user input provided from an external input unit or via a connector having pins in fixed locations at each sensor group that is installed and connected in the communicator 300. Specifically, a type of a bio signal to be processed is determined without a separate authentication process, based on the user input or whether the connector and a corresponding electrode are connected to each other.

In operation 820, a power supply voltage is applied according to the received application information. More specifically, when the method is used to measure an electrocardiogram, for example, a separate power supply voltage is not generated, and when the method is used to measure a skin conductance level, a power supply voltage for generating a constant current is applied. Likewise, when the method is used to measure photoplethysmography, a power supply voltage for generating an LED driving current is applied.

Impedance of each electrode, e.g., of each sensing channel, is measured in operation 830. In operation 831, a constant current is supplied to each sensing channel, and in operation 832, impedance is measured according to each sensing channel.

In operation 840, a value of the measured impedance according to each sensing channel is compared with a predetermined reference value to determine whether an error occurred in the corresponding sensing channel.

When it is determined, in operation 840, that an error has occurred in a particular sensing channel, information about the sensing channel with the error is outputted in operation 850.

In operation 860, a bio signal is measured and analyzed using sensing channels that are determined to be normal, e.g., without errors. In operation 861, an A/D conversion process is performed on a bio signal provided from each sensing channel and, in operation 862, a pre-process, such as filtering and amplification, for example, is performed according to a digital bio signal. In operation 863, an arithmetic algorithm, selected according to an application of the pre-processed bio signal, is performed and, in operation 864, a result of performing the arithmetic algorithm is outputted.

Thereafter, is determined whether to end the method in operation 870, based on whether a bio signal to be measured is still left and, when there is a bio signal left to be measured, operation 861 is performed again, as shown in FIG. 8.

Figure 9:
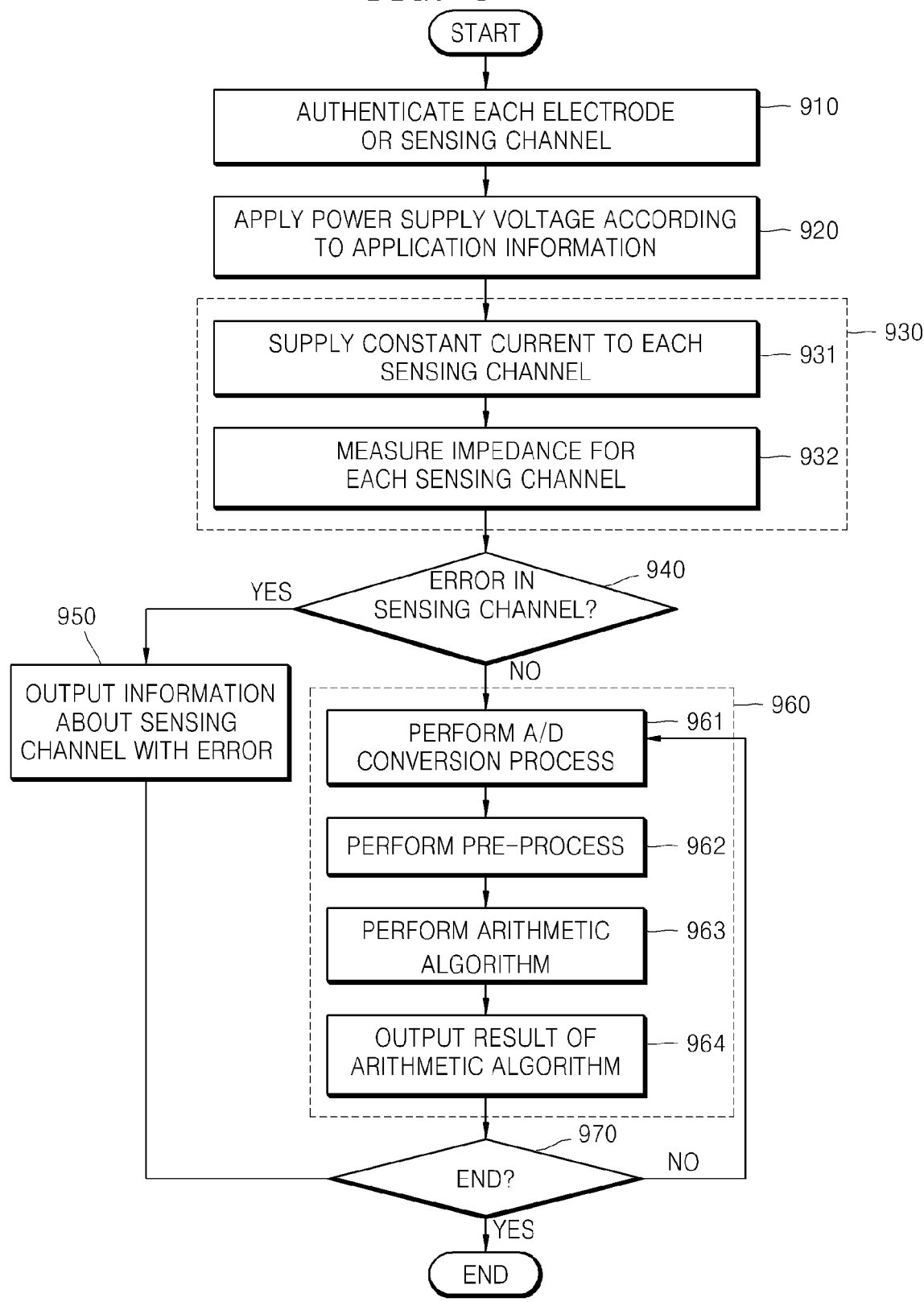
FIG. 9 is a flowchart illustrating an alternative embodiment of a method of integrally processing a plurality of bio signals.

FIG. 9 is a flowchart illustrating an alternative embodiment of a method of integrally processing a plurality of bio signals. The method of FIG. 9 uses the unique ID code information obtained via wire/wireless communication between the sensing module 110 and the communicator 300. Thus, in comparing FIGS. 8 and 9, operation 810 of FIG. 8 is replaced by operation 910, where each electrode or each sensing channel is authenticated. Thus, when the communicator 300 includes a connector, not only a type of a bio signal to be processed is determined, but also the connection of each electrode in a sensor group for measuring a bio signal is determined via operation 910.

Figure 10:
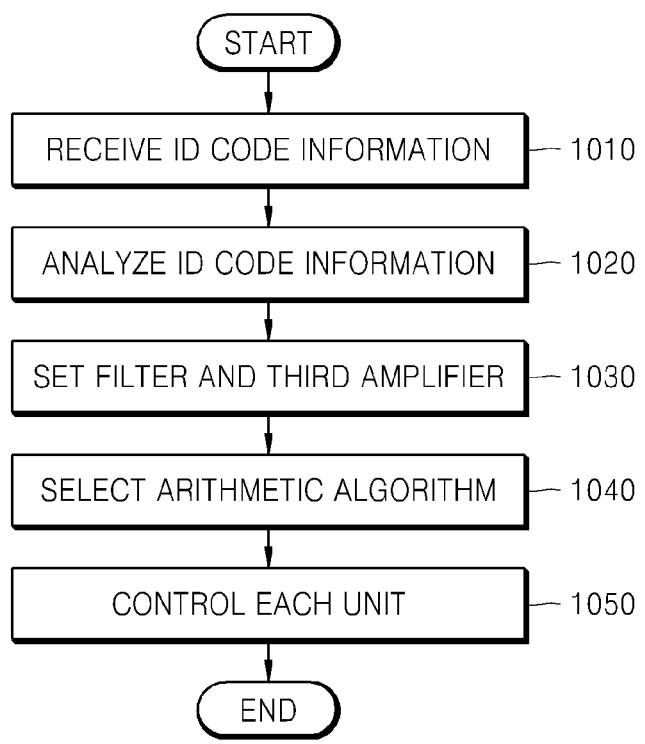
FIG. 10 is a flowchart for describing an embodiment of an operation 910 of the method illustrated in FIG. 9.

FIG. 10 is a flowchart for describing in further detail an embodiment of the operation 910 of the method illustrated in FIG. 9.

Referring to FIG. 10, the authenticator 410 receives the unique ID code information from the communicator 300 in operation 1010.

The received unique ID code information is analyzed in operation 1020. When the unique ID code information is assigned, as illustrated in FIG. 11, for example, a sensor group corresponding to an electrocardiogram is attached when the unique ID code information is "00." Likewise, a sensor group corresponding to an electroencephalogram is attached when the unique ID code information is "01," a sensor group corresponding to a skin conductance level is attached when the unique ID code information is "10," and a sensor group corresponding to a photoplethysmography is attached when the unique ID code information is "11." It will be noted that the operations performed and the unique ID codes shown in FIG. 11 are not limiting, but that alternative embodiments may implement additional types of codes and/or sensor groups than shown in FIG. 11.

Referring again to FIG. 11, in operation 1030, a cutoff frequency of the filter 460 and an amplification gain of the third amplifier 470 are set according to the analyzed unique ID code information. Thus, an optimum processing condition for detecting a bio signal corresponding to the unique ID code information is automatically set.

In operation 1040, an arithmetic algorithm is selected according to the analyzed unique ID code information. Thus, at least one of a plurality of arithmetic algorithms, which are pre-programmed according to an application field of a bio signal corresponding to unique ID code information, is performed according to the analyzed unique ID code information.

In operation 1050, each unit of the first signal processing module 130 and the second signal processing module 150 are controlled according to the analyzed unique ID code information. As a result, when the type of the bio signal is determined (by analyzing the unique ID code information), the first through fourth control signals for controlling the first signal processing module 130 are generated and are outputted. In an embodiment, the first control signal is used to control the first multiplexer 310, the second control signal is used to control the constant current generator 320, the third control signal is used to control the driving current generator 330 and the fourth control signal is used to control the second multiplexer 350. Also, the filter 460, the third amplifier 470 and the operator 480 are controlled based on the set processing condition and selected arithmetic algorithm in operations 1030 and 1040.

FIG. 11 is a block diagram illustrating embodiments of unique ID code information assigned to authenticate an electrode, e.g., a sensing channel in an embodiment of an apparatus and method for integrally processing a plurality of bio signals.

Referring to FIG. 11, when four (4) bio signals are to be measured and analyzed, unique ID code information of 2 bits may be used, as noted above. However, when eight (8) bio signals are to be measured and analyzed, unique ID code information having 3 bits may be used. Put another way, a number of bits of the unique ID code information may be adjusted according to the desired number of bio signals to be measured and analyzed by using one apparatus. Thus, FIG. 11 illustrates an example embodiment wherein the unique ID code information is 2 bits, in which "00" denotes an electrocardiogram, "01" denotes an electroencephalogram, "10" denotes a skin conductance level and "11" denotes a photoplethysmography. Thus, a sensor group used according to each value of the unique ID code is set, and corresponding ID code information may be assigned to an electrode included in each sensor group and/or to each connector of the communicator 300.

For example, when unique ID code information having a value of "00" is received by the authenticator 410 via the communicator 300, the authenticator 410 determines that an electrocardiogram electrode is used, and provides appropriate authentication information to the controller 420. The controller 420 sets a filtering frequency band to be between about 1 Hz and about 150 Hz, which is a frequency band of an electrocardiogram signal, according to the authentication information, while setting an amplification gain, for example, to 1000, and controls each unit so that an arithmetic algorithm is automatically set for a heart rate and arrhythmia monitoring algorithm. Accordingly, when the electrocardiogram electrode is connected, a processing condition that is optimized to the electrocardiogram is automatically set, and the electrocardiogram signal is processed from a bio signal, based on the set processing condition.

Figure 12:
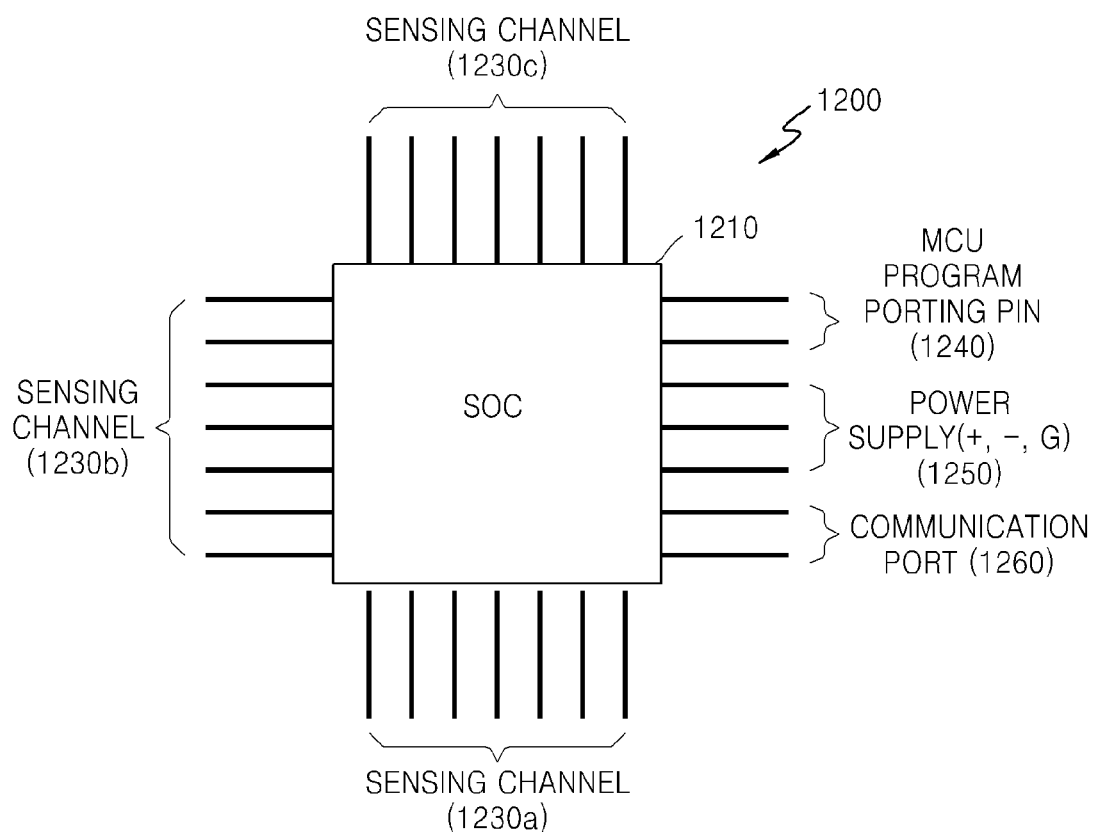
FIG. 12 is a schematic diagram illustrating an embodiment of an apparatus that integrally processes a plurality of bio signals.

FIG. 12 is a schematic diagram illustrating an embodiment of an apparatus that integrally processes a plurality of bio signals. More specifically, FIG. 12 is a schematic diagram illustrating an embodiment of an apparatus that includes a hybrid integrated circuit and which integrally processes a plurality of bio signals.

Referring to FIG. 12, an apparatus 1200 includes an integrated bio signal processing chip, e.g., a SOC 1210, pin groups 1230a, 1230b, and 1230c, which are attached to the SOC 1210 and connected to electrode groups of each sensor group of the sensing module 110, a pin group 1240 attached to the SOC 1210 and used as an MCU program port, a pin group 1250 attached to the SOC 1210 and connected to a power supply source, and a pin group 1260 attached to the SOC 1210 and used as a communication port. A current may be supplied to the sensing module 110 via the pin groups 1230a, 1230b and 1230c, or a bio signal measured in the sensing module 110 may be provided to the first signal processing module 130. An entire control program used by the second signal processing module 150 may be inputted, re-inputted or revised via the pin group 1240. In addition, the apparatus 1200 may be connected to the power supply module 170 via the pin group 1250, and connected to the display module 190 or an external apparatus (not shown) for processing a signal via the pin group 1260.

The apparatus according to the embodiments described herein may be applied to various application fields using bio signals measured and analyzed, as described above. More specifically, for example, an arrhythmia may be detected, a myocardial infarction may be predicted or stress and/or emotional instability may be predicted by analyzing a user's nervous system, by using an electrocardiogram. Also, a user's exercise load may be analyzed using a heartbeat obtained from the electrocardiogram, bio-authentication from electrocardiogram information, and a breathing rate measured via the electrocardiogram. Moreover, consumed calories may be measured based on the electrocardiogram, and sleep may be analyzed based on a heart rate variability obtained from the electrocardiogram. Electromyogram may be used in application fields such as muscle fatigue measurement, muscular strength analysis, calorie measurement and exercise posture correction.

Additionally, an electroencephalogram may be used in application fields such as sleeping depth analysis, epilepsy analysis, concentration and stability analysis, comfort and discomfort analysis, stress analysis, neuropsychology examination, brain diseases analysis, brain-computer interface and lie detection, for example. Electrooculogram may be used in application fields such as eye-computer interface and concentration and stability analysis. Electrogastrography may be used in application fields such as digestion ability analysis or stomach disorder analysis.

Moreover, skin hydration, body fat, an amount of bloodstream, or respiration may be measured by using impedance, and the apparatus may be used in application fields such as stress analysis, lie detection, sensitivity analysis, sleeping analysis, detection of spots on the body suitable for acupuncture and pain spot detection.

When the apparatus uses a bio signal using light, oxygen saturation or a pulse wave may be analyzed. When the apparatus uses motion information obtained from an accelerometer, the apparatus may be used in application fields such as caloric measurement, activities of daily living ("ADL") management, walking analysis and acceleration or angular speed measurement.

The above and other application fields are determined by an arithmetic algorithm included in the second signal processing module 150.

In addition to the above described embodiments, alternative embodiments can also be implemented through computer readable code/instructions in/on a medium, e.g., a computer readable medium, to control at least one processing element to implement any above described embodiment. The medium can correspond to any medium/media permitting the storing and/or transmission of the computer readable code.

The computer readable code can be recorded/transferred on a medium in a variety of ways, with examples of the medium including recording media, such as magnetic storage media, e.g., read only memory ("ROM"), floppy disks, hard disks, etc., and/or optical recording media, such as compact disk read only memory ("CD-ROM") or digital versatile disk ("DVD"), for example, and transmission media such as carrier waves, as well as through the Internet, for example. Thus, the medium may further be a signal, such as a resultant signal or bit stream, according to one or more embodiments. The media may also be a distributed network, so that the computer readable code is stored/transferred and executed in a distributed fashion. Still further, as only an example, the processing element could include a processor or a computer processor, and processing elements may be distributed and/or included in a single device.

The present invention should not be construed as being limited to the embodiments set forth herein. Rather, these embodiments are provided so that this disclosure will be thorough and complete and will fully convey the general inventive concept to those skilled in the art.

While the present invention has been particularly shown and described with reference to embodiments thereof, it will be understood by those of ordinary skill in the art that various changes in form and details may be made therein without departing from the spirit or scope of the present invention as defined by the following claims.

What is claimed is:

1. An apparatus for integrally processing a plurality of biologic signals, the apparatus comprising:
    a first signal processing module which generates a signal for operating a sensing module including a plurality of sensor groups which measures the plurality of biologic signals, and which processes a biologic signal provided from the plurality of sensor groups based on a control signal; and
    a second signal processing module which authenticates a sensor group from among the plurality of sensor groups, generates the control signal according to a result of the authentication while automatically setting a processing condition, processes the biologic signal provided from the first signal processing module according to the processing condition and outputs a result of processing the biologic signal.

2. The apparatus of claim 1, wherein the plurality of sensor groups comprises at least one of a first sensor group which measures a biologic potential signal, a second sensor group which measures an impedance signal and a third sensor group which measures a biologic signal using light.

3. The apparatus of claim 1, wherein the processing condition comprises at least one of a filtering frequency band, an amplification gain and an arithmetic algorithm.

4. The apparatus of claim 1, wherein the first signal processing module and the second signal processing module are a hybrid integrated circuit implemented as a system on chip.

5. The apparatus of claim 1, wherein unique identification code information corresponding to a type of biologic signal is assigned to each sensor group of the plurality of sensor groups.

6. The apparatus of claim 1, wherein
    the sensing module further includes:
        a first sensor group which measures a biologic potential signal; and
        a second sensor group which measures a biologic signal using light, the first signal processing module and the second signal processing module generate biologic information for monitoring a patient by processing a plurality of biologic potential signals and a plurality of biologic signals using light, and the first signal processing module and the second signal processing module are a hybrid integrated circuit implemented as a system on chip.

7. The apparatus of claim 1, wherein the sensing module further includes:
    a first sensor group which measures a biologic potential signal; and
    a second sensor group which measures an impedance signal,
    the first signal processing module and the second signal processing module process a plurality of biologic potential signals and a plurality of impedance signals and generate biologic information corresponding to a result of the process, and
    the first signal processing module and the second signal processing module are a hybrid integrated circuit implemented as a system on chip.

8. The apparatus of claim 1, wherein
the sensing module further includes a first sensor group for measuring a biologic potential signal,
    the first signal processing module and the second signal processing module process a plurality of biologic potential signals and generate biologic information corresponding to a result of the process, and
    the first signal processing module and the second signal processing module are a hybrid integrated circuit implemented as a system on chip.

9. The apparatus of claim 1, wherein the first signal processing module comprises a communicator which receives unique ID information transmitted from each of the plurality of sensor groups wirelessly or via wires, and transmits the received unique ID code information to the second signal processing module.

10. A method of integrally processing a plurality of biologic signals, the method comprising:
    generating a signal for operating each sensor group of a plurality of sensor groups of a sensing module which measures the plurality of biologic signals and processes a biologic signal provided from each of the sensor groups based on a control signal;
    authenticating a sensor group used from among the plurality of sensor groups;
    generating the control signal according to a result of the authenticating while automatically setting a processing condition;
    processing a provided biologic signal according to the processing condition; and
    outputting a result of the processing.

11. The method of claim 10, wherein the sensing module comprises at least one of a first sensor group which measures a biologic potential signal, a second sensor group which measures an impedance signal and a third sensor group which measures a biologic signal using light.

12. The method of claim 10, wherein the processing condition comprises at least one of a filtering frequency band, an amplification gain and an arithmetic algorithm.

13. The method of claim 10, wherein unique identification code information corresponding to a type of a biologic signal is assigned to each of sensor group of the plurality of sensor groups.

14. The method of claim 10, wherein
the sensing module comprises:
    a first sensor group which measures a biologic potential signal; and
    a second sensor group which measures a biologic signal using light, and
the processing the provided biologic signal comprises generating biologic information for monitoring a patient by processing a plurality of biologic potential signals and a plurality of biologic signals using light.

15. The method of claim 10, wherein
the sensing module comprises:
    a first sensor group which measures a biologic potential signal; and
    a second sensor group which measures an impedance signal, and
the processing the provided biologic signal comprises:
    processing a plurality of biologic potential signals and a plurality of impedance signals are processed; and
    generating biologic information corresponding to a result of the processing the plurality of biologic potential signals and the plurality of impedance signals.

16. The method of claim 10, wherein
the sensing module comprises a first sensor group for measuring a biologic potential signal, and
the processing the provided biologic signal comprises:
    processing a plurality of biologic potential signals; and
    generating biologic information corresponding to a result of the processing the plurality of biologic potential signals.

17. A computer program product, comprising:
a non-transitory storage medium having computer readable program code stored thereon for executing a method of integrally processing a plurality of biologic signals; and
instructions for causing a computer to implement the method, the method comprising:
    generating a signal for operating each sensor group of a plurality of sensor groups of a sensing module which measures the plurality of biologic signals and processes a biologic signal provided from each of the sensor groups based on a control signal;
    authenticating a sensor group used from among the sensor groups of the plurality of sensor groups;
    generating the control signal according to a result of the authenticating while automatically setting a processing condition;
    processing a provided biologic signal according to the processing condition; and
    outputting a result of the processing.

* * * * *